United States Patent
Ritter (10) Patent No.: US 12,194,217 B2
(45) Date of Patent: Jan. 14, 2025

(54) BLOOD TREATMENT MACHINE WITH AUTOMATIC FILL LEVEL MONITORING AND CONTROL OF AN AIR SEPARATOR BY MEANS OF PRESSURE PULSE FREQUENCY ANALYSIS

(71) Applicant: B. Braun Avitum AG, Melsungen (DE)

(72) Inventor: Kai-Uwe Ritter, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 378 days.

(21) Appl. No.: 17/781,321

(22) PCT Filed: Dec. 3, 2020

(86) PCT No.: PCT/EP2020/084542
§ 371 (c)(1),
(2) Date: May 31, 2022

(87) PCT Pub. No.: WO2021/110874
PCT Pub. Date: Jun. 10, 2021

(65) Prior Publication Data
US 2023/0001066 A1   Jan. 5, 2023

(30) Foreign Application Priority Data
Dec. 4, 2019   (DE) .................. 10 2019 133 075.0

(51) Int. Cl.
*A61M 1/36*   (2006.01)
(52) U.S. Cl.
CPC ....... *A61M 1/3624* (2013.01); *A61M 2205/18* (2013.01); *A61M 2205/3331* (2013.01); *A61M 2205/3389* (2013.01)
(58) Field of Classification Search
CPC ............ A61M 1/3624; A61M 2205/18; A61M 2205/3331; A61M 2205/3389; A61M 1/3627
See application file for complete search history.

(56) References Cited

U.S. PATENT DOCUMENTS

| 6,745,630 B2 | 6/2004 | Gross |
| 8,718,957 B2 | 5/2014 | Furmanski et al. |

(Continued)

FOREIGN PATENT DOCUMENTS

| JP | 2002301148 A | 10/2002 |
| JP | 2011516229 A | 5/2011 |

(Continued)

OTHER PUBLICATIONS

Search Report received in German Application No. 10 2019 133 075.0 dated Sep. 10, 2020, with translation, 13 pages.

(Continued)

*Primary Examiner* — Thuan D Dang
(74) *Attorney, Agent, or Firm* — Christopher A. Rothe; CM Law (57) ABSTRACT

A blood treatment device for extracorporeal blood treatment and a method for monitoring the fill level of blood with the blood treatment device. The device includes at least one blood conducting system and at least one chamber container for separating bubbles from the blood to be treated. The device further includes a blood pumping device designed to pump the blood and generate pressure pulses with a predefined frequency in the blood conducting system. The blood treatment device additionally has at least one pressure detection sensor for capturing the pressure pulse introduced by the blood pumping device and a data processing unit designed to derive a fill level parameter from the pressure pulse captured and to modify the state of an information signal as a function of the fill level parameter. At least one alarm device is activated as a function of the state of the information signal.

16 Claims, 6 Drawing Sheets

(56)  References Cited

U.S. PATENT DOCUMENTS

| | | |
|---|---|---|
| 9,795,731 B2 | 10/2017 | Kelly et al. |
| 2009/0230036 A1 | 9/2009 | Apel et al. |
| 2013/0006130 A1* | 1/2013 | Olde .................. A61M 1/3659 |
| | | 600/504 |
| 2013/0049974 A1 | 2/2013 | Crnkovich |
| 2015/0238681 A1 | 8/2015 | Vasta et al. |
| 2016/0310657 A1 | 10/2016 | Solem et al. |
| 2017/0333616 A1 | 11/2017 | Vasta |

FOREIGN PATENT DOCUMENTS

| | | |
|---|---|---|
| WO | 9301858 A1 | 2/1993 |
| WO | 2006122737 A1 | 11/2006 |
| WO | 2015188154 A9 | 12/2015 |

OTHER PUBLICATIONS

Search Report received in International Application No. PCT/EP2020/084542 dated Mar. 5, 2021, with translation, 8 pages.
Written Opinion received in International Application No. PCT/EP2020/084542 dated Mar. 5, 2021, with translation, 12 pages.
Office Action received in Japanese Application No. 2022-532118 dated Sep. 3, 2024, with translation, 8 pages.

* cited by examiner

Fig. 6

BLOOD TREATMENT MACHINE WITH AUTOMATIC FILL LEVEL MONITORING AND CONTROL OF AN AIR SEPARATOR BY MEANS OF PRESSURE PULSE FREQUENCY ANALYSIS

CROSS-REFERENCE TO RELATED APPLICATIONS

This application is the U.S. national stage entry of International Application No. PCT/EP2020/084542, filed Dec. 3, 2020, and claims priority to German Application No. 10 2019 133 075.0, filed Dec. 4, 2019. The contents of International Application No. PCT/EP2020/084542 and German Application No. 10 2019 133 075.0 are incorporated by reference herein in their entireties.

FIELD

The present invention relates to a blood treatment device for extracorporeal blood treatment, comprising at least one blood conducting system/blood line system and at least one chamber container for separating bubbles from the blood to be treated, comprising a blood pumping device configured to pump the blood and to generate pressure pulses with a predefined frequency in the blood conducting system. Furthermore, the invention relates to a method for monitoring the fill level of the blood in the blood treatment device.

BACKGROUND

Extracorporeal blood treatment machines have been known for a long time in the prior art. For example, WO 93/01858 A discloses a blood treatment machine having a control unit that outputs a signal for closing a venous tube clamp when air/gas is detected in a venous portion of the extracorporeal blood circuit. The air is removed from the venous portion by inserting a sterile syringe into a vent line of a filter of an air collection chamber, opening a valve in the vent line, and sucking out the air.

Additionally, U.S. Pat. No. 9,795,731 B2 discloses an extracorporeal blood treatment machine with a control unit. According to this document, air is removed from a venous portion of an extracorporeal blood circuit via a blood pump. Furthermore, reference is made to WO 2006/122737 A1, known from the prior art, which discloses a method for air-free filling of the blood side of a hemodialysis device with a physiological electrolyte solution. Additionally, US 20133/0049974 A1 is known, which discloses early detection of a low bicarbonate level. Furthermore, document WO 2015/188154 A9 is known from the prior art, which discloses a system for calculating a change in the fluid in a pump chamber.

Basically, it is necessary to degas extracorporeal blood before it is returned from the extracorporeal blood circuit to a patient. I.e., if air is present in the venous portion of an extracorporeal blood circuit, this basically presents a dangerous situation for the patient. Therefore, it is known from the prior art that air which is in the venous portion of the extracorporeal blood circuit has to be removed, wherein a blood treatment therapy is to be continued only after the removal.

Therefore, as a rule, the above-mentioned air separator is interposed in particular in the venous line portion of the extracorporeal blood conducting system. This normally has a chamber into which blood is filled up to a certain filling height in such a way that a hollow space remains above the blood level/gage formed in this way, into which the air contained in the blood can outgas and can then escape via an outlet opening. It is also well known that this outgassing process leads to a drop in the fill level gage or, respectively, the blood level in the chamber to such an extent that the opening of a blood filler neck inside the chamber comes to lie above the lowered blood level/gage. This in turn can cause air bubbles or foam to form in the chamber of the air separator as a result of the blood now dripping in, which impairs the actual air separation function or causes it to fail, which in turn may lead to an alarm being triggered by a microbubble detector downstream of the chamber. It is therefore known from the prior art that gage detectors are also used to solve this problem, which monitor the current gage level in the air separator in such a way that the opening of the blood filler neck is below the blood level/gage.

However, the devices disclosed in the prior art have the disadvantage that air removal/separation/degassing from the blood present in the venous line portion is relatively complicated and inconvenient, and thus not user-friendly. Furthermore, in the known prior art, numerous specific sensors are used, such as elaborate air detectors that detect whether there is air in the system which is dangerous for the patient, and fill level sensors that detect whether the fill level of the air separator chamber is sufficient. This makes the entire sensor system complicated and expensive.

SUMMARY

It is therefore the object of the invention to avoid or at least reduce the disadvantages of the prior art. In particular, the blood treatment machine is to be designed in such a way that the gage level in the venous chamber can be easily estimated.

The core idea of the present invention essentially consists in that the blood treatment device additionally comprises at least one pressure detection sensor for detecting the pressure pulse introduced by the blood pumping device, a data processing unit which is adapted/designed to derive a fill level parameter from the detected pressure pulse and to change the state of a notification signal as a function thereof, and at least one alarm device which is activated as a function of/depending on the state of the notification signal.

So, utilize/use pressure pulses, which are generated by a blood pump/blood pumping device when conveying blood in the extracorporeal blood circuit and are input into the conveyed blood, in order to determine or respectively estimate the current fill level.

Here, the technical effect is utilized that these (inevitably generated) pressure pulses within an air separator chamber are changed depending on the current fill level and the resulting current air cushion volume above the blood gage/blood level within the air separator. This/These sensor-detectable change(s), for example in the pulse amplitude, allow(s) (continuous) conclusions to be drawn about the current fill level.

In other words, the object is solved in a generic blood treatment device in that the blood treatment device comprises at least one pressure detection sensor, which is generally provided for detecting the blood pressure generated by a blood pump/blood pumping device of the treatment device in the venous blood conducting system, in particular in the air separator chamber. According to the invention, the pressure detection sensor is now (additionally) utilized/used for detecting at least one fill level parameter of the pressure pulse introduced by the blood pumping device, wherein a data processing unit is provided which is designed to change the state of a notification or warning signal into a relevant state depending on the at least one fill level parameter of the pressure pulse detected by the pressure detection sensor, for which purpose an alarm device is provided which is activated in case of a relevant state of the notification signal.

Thus, in a first embodiment, the notification signal can assume a relevant and an irrelevant state, i.e., it can be switchable between two binary states. In a further embodiment, the notification signal can be continuously variable, i.e. change its state slowly, i.e. continuously.

The extracorporeal blood treatment device advantageously comprises the pressure detection sensor, which is designed/adapted to indirectly measure the fill level of the chamber container/air separator chamber. The pressure detection sensor thus detects a fill level parameter that represents a value for the gage level of the chamber container. In a further advantageous manner, the blood treatment device according to the invention additionally comprises the data processing unit, which sets the state of a notification signal to a relevant or a non-relevant state depending on the detected fill level parameter. The notification signal sets the furthermore provided alarm device to an activated or deactivated state. Thus, apart from the pressure detection sensor (which may be present anyway), no other sensor is provided in the blood treatment device to detect the level in the air separator. In an advantageous manner, the blood pumping device, which is inevitably required to pump the blood through the dialysis device, is also used to raise the fill level inside the chamber container again in the event of a drop. For this purpose, a ventilation opening on the chamber has to be opened automatically in order to remove the excess air in a targeted manner. The prior art are roller pumps that can remove or add air to adjust the gage, or small 'compressors' that provide overpressure and valves to release air.

In a preferred embodiment, the at least one fill level parameter comprises at least the pressure pulse amplitude and/or the pressure pulse width of the pressure pulse detected by the pressure detection sensor. By determining the pressure pulse amplitude or respectively the pressure pulse width of the pressure pulse detected by the pressure detection sensor, the attenuation present in the system (influenced by the air cushion volume in the air separator) can be determined in an advantageous manner, via which the fill level of the air separator or the amount of air present in the air separator/chamber container is indirectly determined. The pressure pulse amplitude and/or the pressure pulse width are the characteristic values to describe the pressure pulse.

In a further preferred embodiment, the data processing unit is configured to perform a frequency analysis method, preferably via Fourier transformation, to determine the pressure pulse amplitude (hereinafter only referred to as pressure amplitude) and the pressure pulse width (hereinafter only referred to as pressure width) from the pressure pulse. In this frequency analysis method, the periodic functions are split into a sum of angular functions. The period of a single oscillation or respectively of a harmonic is then an integer multiple of a fundamental oscillation with the period and the angular frequency. The amplitudes of these oscillations are called Fourier coefficients. From a mathematical point of view, this is a series expansion. With this method, it is advantageously possible to represent a measured signal by its individual frequency components and to obtain a frequency spectrum. By converting the sine or cosine components of the same frequency into polar coordinates, an amplitude and a phase spectrum are obtained.

Further advantageously, the fill level parameter represents a measure of the fill level of the blood in the chamber container and the data processing unit is adapted to change the notification signal to a relevant state as soon as the fill level parameter falls below a predefined fill level threshold. By determining the fill level parameter, the pressure amplitude and the pressure width of the pressure pulse detected by the pressure detection sensor is determined, whereby the volume of air in the chamber container is estimated via the attenuation. If the fill level parameter falls below a predefined fill level threshold, i.e. the gage in the chamber container falls below a defined mark, the notification signal is set to a relevant—i.e. a critical—state.

In a further embodiment, the data processing unit is additionally adapted to change an alarm signal to a relevant state and to activate at least the alarm device as soon as a predefined occurrence threshold, which defines how often the fill level of the blood in the chamber container falls below the fill level threshold in a predefined time interval, is exceeded. In an advantageous manner, the blood pumping device is driven so as to increase the blood gage within the chamber container as soon as the gage of the blood in the chamber container falls below the fill level threshold. In this way, it is advantageously effected that no air bubbles are introduced into the blood conducting system.

Further advantageously, the pressure detection sensor has a sampling rate of at least 100 Hz in order to detect the pressure pulse of the blood over time. This is preferably a normal venous pressure sensor which indirectly detects the pressure in the blood line system either via TP (Transducer Protector Filter) or via PODs.

In a further advantageous embodiment, the blood pumping device additionally comprises a gage and/or level regulation pump. By this configuration, a further pump is provided, which is configured to keep the level or gage in the blood conducting system or in the chamber container constant, respectively, so that the gage does not fall below a critical value.

Further advantageously, a method for monitoring the fill level of blood in a blood treatment device according to the invention includes the following steps:
- detecting the pressure pulse introduced by the blood pumping device by the pressure detection sensor;
- deriving a fill level parameter from the pressure pulse detected by the pressure detection sensor,
- continuously analyzing and processing the detected fill level parameter by the data processing unit;
- changing the state of a notification signal in dependence of the fill level parameter as soon as it falls below a predefined fill level threshold, and
- activating the alarm device depending of the state of the notification signal.

The basic idea of the device according to the invention is to estimate the air volume in the chamber container via the determined attenuation, wherein the attenuation changes when foam or air is present in the blood conducting system or the chamber container. Thus, in an advantageous way, no additional fill level sensor is needed, but the detected fill level parameters are determined indirectly by evaluating the pressure pulse of the blood pumping device, since the pressure pulse is present in the blood conducting system of the blood treatment device anyway. The amount of foam is thus also detected and determined.

In a further advantageous method step, a continuous determination of the pressure amplitude and/or of the pressure width from the pressure pulse via a frequency analysis method by the data processing unit is provided. The data processing unit is thus a continuously operating processor in combination with a memory unit, which continuously acquires the provided data, parameters, reference values and the predefined thresholds, evaluates them, assesses them and provides them to other units, for example the alarm device.

Further advantageously, the method comprises the following steps:
changing the notification signal to a relevant state as soon as the fill level parameter falls below a predefined fill level threshold;
generating a drive signal in the event of a relevant state of the notification signal; and
driving the blood pumping device in such a way that the fill level of the blood in the chamber container is increased as soon as the predefined fill level is undershot/has fallen below.

As soon as the fill level threshold, i.e. the gage level of the blood in the chamber container, falls below a predefined fill level threshold, i.e. a predefined threshold, which would pose a risk to the patient if the blood gage fell below the predefined threshold, a notification signal is generated by the data processing unit. From this notification signal, the data processing unit in turn generates a drive signal, which drives the blood pumping device and the gage adapting device in such a way that they increase the fill level of blood in the chamber container, so that the risk of air getting into the patient's blood and causing damage is averted. Overall, the method according to the invention thus provides a control method which continuously ensures that there is sufficient blood in the blood conducting system and the chamber container, which is sufficiently free of air and which has such a high gage level that the patient is continuously supplied with sufficient blood.

Further advantageously, the method comprises the following steps:
driving the gage and/or level regulation pump and the ventilation opening of the chamber container as soon as the predefined fill level threshold is undershot. The gage and/or level regulation pump is thus additionally designed to maintain the fill level in the chamber container at a predefined gage and/or level. Furthermore, the ventilation opening is opened to remove excess air so that the entire blood circuit is vented.

In a further advantageous embodiment, the method comprises the following steps:
changing the state of an alarm signal to a relevant state as soon as the fill level threshold exceeds a predefined occurrence threshold, and
activating the alarm device in case of a relevant state of the alarm signal.

If the system is forced to frequently adjust the fill level of the blood, i.e. if air is frequently present in the blood, an alarm signal is triggered, which activates the alarm device. In this case, the system is affected by a leak, a leakage or another technical problem, about which the qualified personnel must be informed. If air is detected in the blood conducting system, the data processing unit stops the blood pump and issues an alarm signal via the alarm device.

In other words, the invention relates to a dialysis machine comprising a pressure sensor, wherein the latter measures the pressure curve, which determines the pressure in the chamber, with high resolution. The frequency is chosen such that pressure pulses, which are generated by the peristalsis of the blood pump, can still have good resolution. The pressure pulse, height, width and attenuation are determined via frequency analysis, in particular Fourier transform. A small volume means that the chamber container is full. This in turn means a higher frequency component, i.e. a higher and shorter pulse. A large volume means that the chamber container is empty, i.e. a higher basic component of the frequency and a more attenuated and delayed signal. A reference value is either permanently stored or is only (fully) defined after filling.

If the deviation is greater than X, i.e. if the spectrum and amplitudes change beyond limits, an alarm is issued before the chamber is completely empty. Alternatively, it is also possible that the gage is automatically readjusted. If this readjustment occurs too often, an alarm will still be issued since there is an air intake somewhere or the system is leaking or respectively damaged. In another alternative, a certain, known amount of air is introduced via the connection for gage increase or gage lowering with the existing blood pump and closed venous clamp. From the resulting increase in pressure, the volume of air in the chamber can be determined directly. This can be done via the device for gage increase and gage lowering, which has a pump. In addition, it is provided to detect certain bloodlines as the spectrum changes depending on the chamber size and the chamber material.

The pressure sensor is a normal venous pressure sensor that indirectly records the pressure in the venous line either via TP (Transductor Protector Filter) or via PODs. The sampling rate of the sensor has to be in the range of about 100 Hz sampling rate to resolve the pulses sufficiently accurately.

The method steps of foam detection work in such a way that the air volume in the chamber is estimated via the attenuation, since foam behaves differently than pure blood or respectively has a different attenuation coefficient.

Preferably, the data processing unit is adapted to determine an attenuation of the pressure pulse as a further fill level parameter from the detected pressure pulse and to compare it with an associated reference value stored in the data processing unit.

According to a further preferred embodiment, a maximum pressure pulse width and/or a minimum pressure pulse amplitude can be stored as a reference value; or a minimum pressure pulse width and/or a maximum pressure pulse amplitude can be stored and, when the minimum value is compared and undershot and/or the maximum value is exceeded, the data processing unit changes the state of the notification signal accordingly. In this way, for example, a maximum pressure pulse width can serve as a threshold, so that when this threshold is exceeded, the data processing device recognizes and determines that a fill level height is too low. Since, for example, a high fill level height of the blood in the chamber has a smaller pressure pulse width than a low fill level height, the associated fill height, or in particular the associated lower fill level limit for safe operation of the drip chamber, can be inferred on the basis of the associated fill level parameter when a predefined threshold is exceeded or undershot.

Preferably, the data processing unit can additionally be adapted to change the state of the notification signal and to activate at least the alarm device as soon as a predefined occurrence threshold, which defines how often the fill level of the blood in the chamber container falls below a fill level threshold in a predefined time interval, is exceeded.

There are various definitions for a (pressure) pulse width. For example, one definition of pulse width refers to the time of a pulse that lies between the 50% values from the rising and falling pulse edges. The 50% value, Full Width at Half Maximum (FWHM), refers to the maximum amplitude value of the pulse. Another definition, for example, uses the 90% value or 1/e, with e=2.718 of the maximum amplitude value.

A frequency amplitude is an amplitude of a frequency in the frequency spectrum. A frequency range amplitude is an amplitude of a predetermined range of frequencies, such as from a specified minimum frequency to a specified maximum frequency.

In other words, a method for monitoring the fill level of blood in a blood treatment device may in particular comprise the following steps: detecting the pressure pulse introduced by the blood pumping device by the pressure detection sensor; deriving a fill level parameter from the pressure pulse detected by the pressure detection sensor, continuously analyzing and processing the detected fill level parameter by the data processing unit; changing the state of a notification signal in dependence of the fill level parameter as soon as it falls below a predefined fill level threshold and activating the alarm device in dependence of the state of the notification signal.

According to one embodiment, the method may comprise the following steps: changing the notification signal to a relevant state as soon as the fill level parameter falls below a predefined fill level threshold; generating a drive signal in case of a relevant state of the notification signal and driving the blood pumping device so that the fill level of the blood in the chamber container is increased as soon as the fill level falls below the predefined fill level threshold.

Preferably, the method may comprise the step of: driving the gage and/or level regulation pump and the ventilation opening of the chamber container as soon as the fill level falls below the predefined fill level threshold.

BRIEF DESCRIPTION OF THE DRAWING FIGURES

The invention is further explained below with the aid of the following figures. The following is shown.

DETAILED DESCRIPTION

Figure 1:
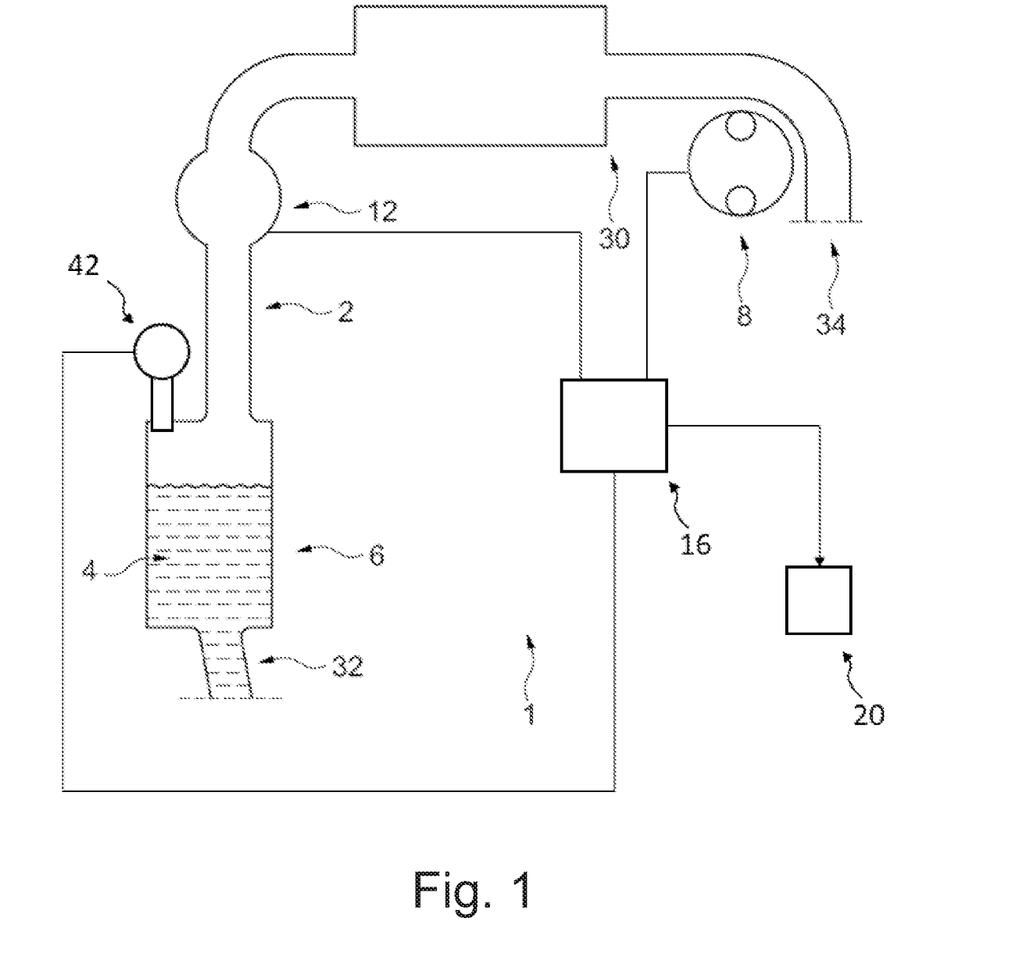
FIG. 1 shows a blood treatment device according to the present invention with an approximately full chamber container.

FIG. 1 shows a blood treatment device 1 comprising a blood conducting system 2 having blood 4 in its chamber container 6. It can be clearly seen that the chamber container 6 is filled to approximately three quarters of the maximum fill level with blood 4. Furthermore, the blood treatment device 1 comprises a blood pumping device 8, preferably a peristaltic pump, which circulates the blood 4 in the blood conducting system 2. Furthermore, a pressure detection sensor 12 can be seen integrated in the blood conducting system 2. However, the pressure detection sensor 12 may also be provided on the chamber container 6. Furthermore, the input 32 of the chamber container 6 and the output 34 of the blood conducting system 2 can be seen. The blood treatment device 1 shown depicts the pressure detection sensor 12 being connected to the data processing unit 16 in a signal-conducting manner, wherein the signal conduction can take place unidirectionally as well as bidirectionally, i.e. the pressure detection sensor 12 sends detected signals to the data processing unit 16, but the latter can also send signals back to the pressure detection sensor 12. Furthermore, it is shown that both the blood pumping device 8 and the alarm device 20 are connected to the data processing unit 16 in a signal-conducting manner. In all cases, the signal conduction may be unidirectional or bidirectional. The alarm device 20 may, for example, also be designed as a mobile communication device, e.g. a tablet and/or cell phone.

Figure 2:
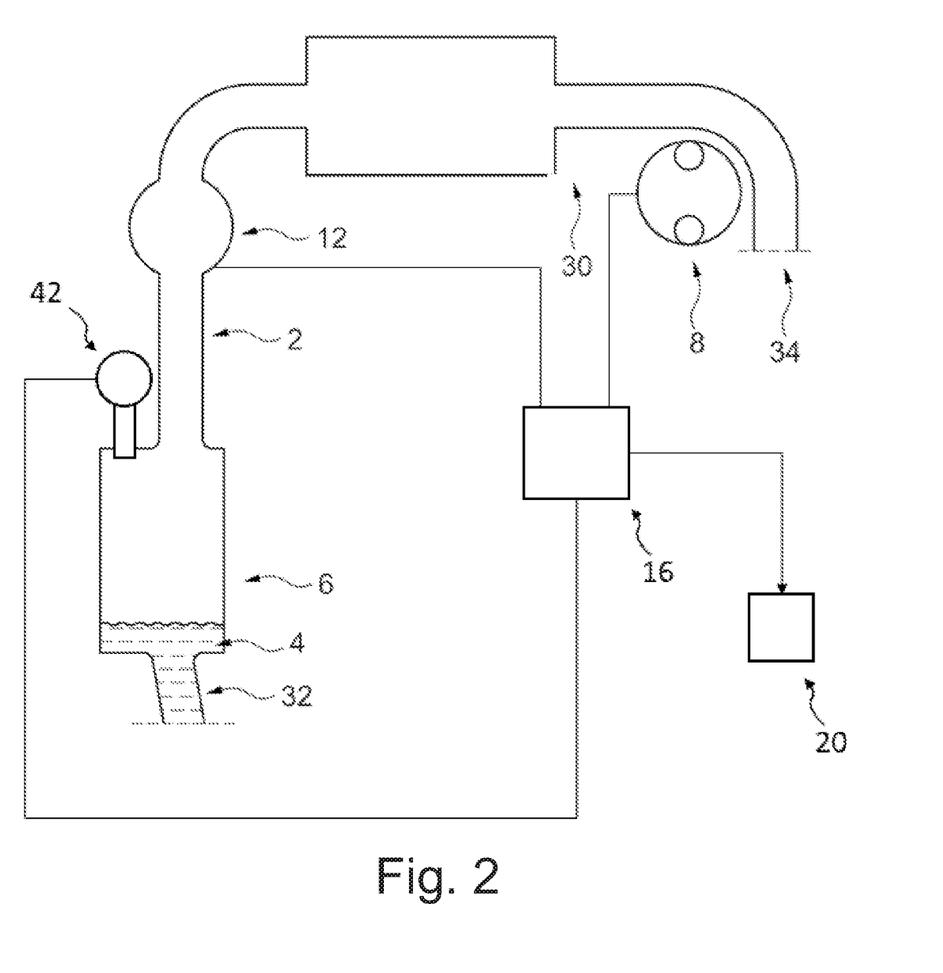
FIG. 2 shows a blood treatment device according to the present invention with an approximately empty chamber container.

FIG. 2 shows another state of the blood treatment device 1, in which the chamber container 6 is approximately empty and not filled with blood 4. Again, the blood pumping device 8 and the pressure detection sensor 12 can be seen, which is integrated in the blood conducting system 3. The blood conducting system 2 again has an input 32 and an output 34. FIG. 2 also shows the signal conducting connection of the data processing unit 16 to the blood pumping device 8, the pressure detection sensor 12 and the alarm device 20. The blood pumping device 8 may additionally have a gage and/or a level regulation pump 42, which is explicitly designed to maintain the fill level at a predetermined level.

Figure 3A:
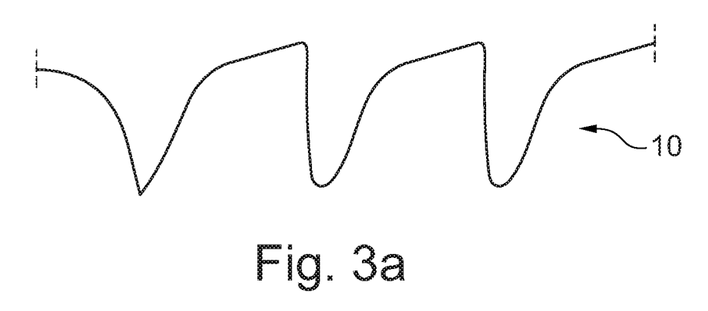
FIG. 3a shows a pressure curve over time of a pressure pulse.
Figure 3B:
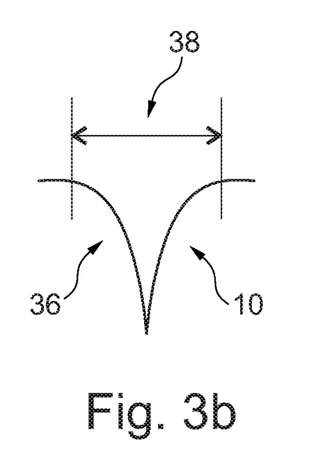
FIG. 3b shows a pressure pulse measured by a pressure detection sensor and processed by a data processing unit.
Figure 3C:
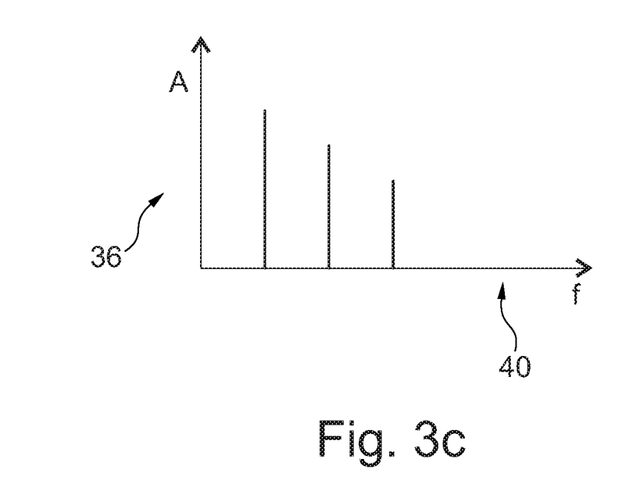
FIG. 3c shows a frequency spectrum which has a pressure amplitude plotted on its ordinate and a frequency plotted on its abscissa.

FIG. 3 is divided into the individual FIGS. 3a, 3b and 3c. FIG. 3a shows a pressure curve over time of the pressure pulse 10, which is provided by the blood pumping device 8 or a further pressure pulse source. The further pressure pulse source can also be arranged externally, for example. FIG. 3b shows a pressure pulse 10 measured in this way by the pressure detection sensor 12 and processed by the data processing unit 16. The measured pressure pulse 10 has a pressure amplitude 36 and a pressure width 38. FIG. 3c shows a frequency spectrum which has a pressure amplitude 36 plotted on its ordinate and a frequency 40 plotted on its abscissa. FIG. 3b and FIG. 3c are examples of a fully filled chamber container, since the pressure pulse 10 is 'sharp' and has a large pressure amplitude 36. This can also be seen in the high pressure amplitude 36 of the frequency spectrum.

Figure 4A:
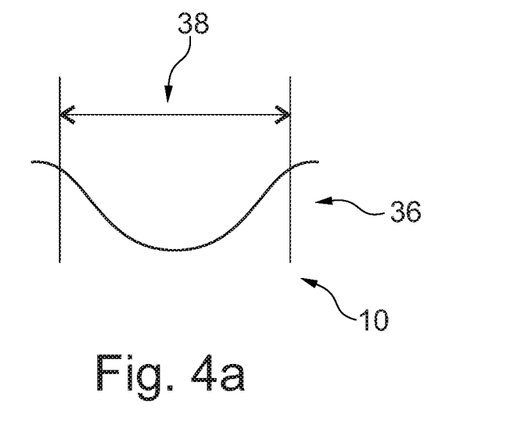
FIG. 4a shows a pressure pulse measured by a pressure detection sensor, which has a wide pressure pulse with a small pressure amplitude.
Figure 4B:
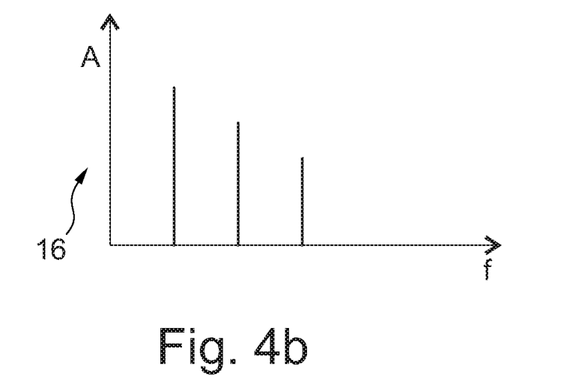
FIG. 4b shows a frequency spectrum representing a measured pressure pulse which has a pressure amplitude plotted on the ordinate and a frequency plotted on the abscissa.

FIG. 4 is divided into FIG. 4a and FIG. 4b. FIG. 4a shows a pressure pulse 10 measured by the pressure detection sensor 12, which has a wide pressure pulse 38 with a small pressure amplitude 36. The measured pressure pulse is represented by the frequency spectrum shown in FIG. 4b, wherein again the pressure amplitude 36 is shown on the ordinate and the frequency f is shown on the abscissa.

Figure 5:
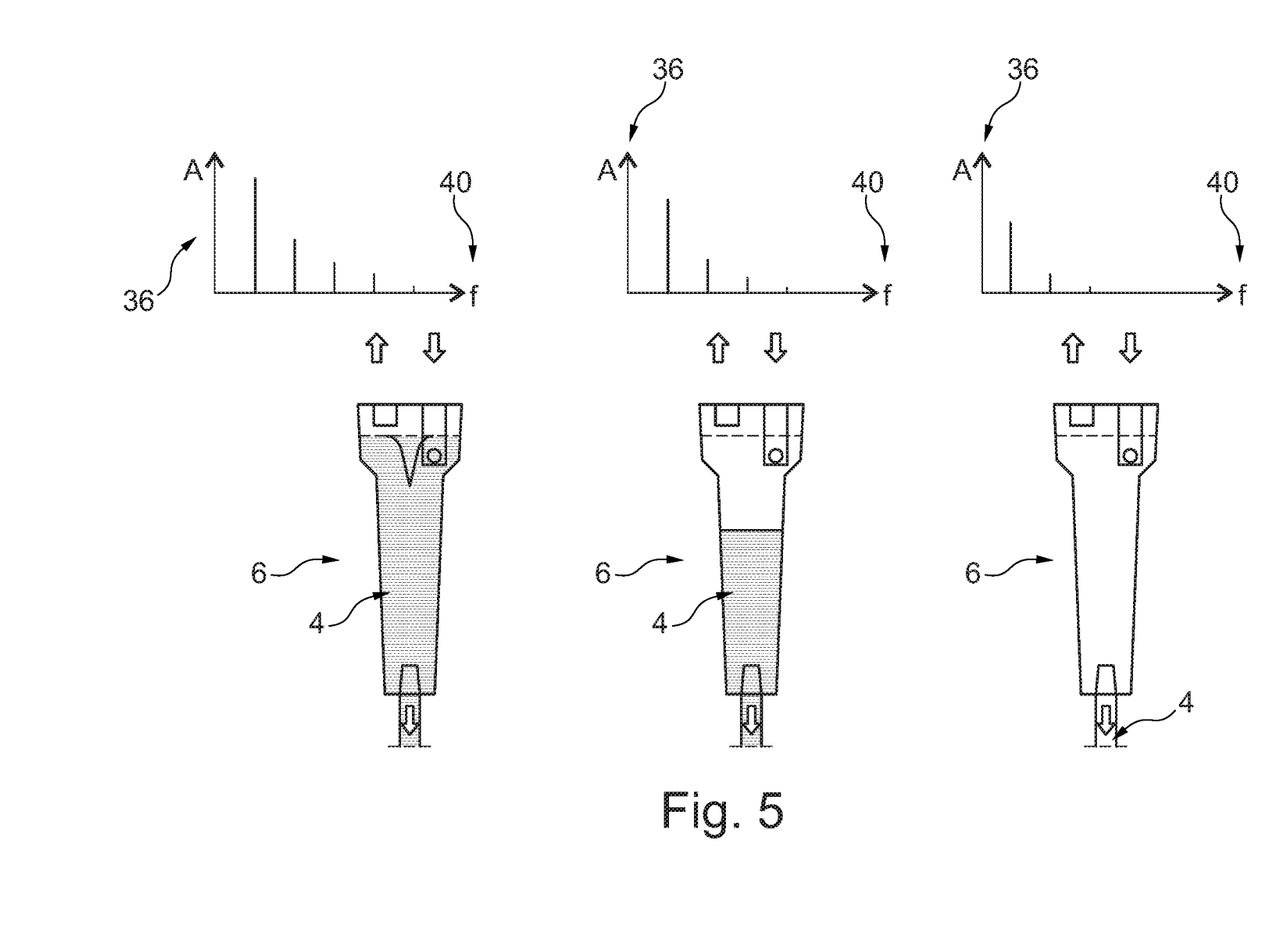
FIG. 5 shows various frequency spectra representing the corresponding fill levels of the respective chamber containers.

FIG. 5 shows three different fill states of the chamber container 6. In the first fill state, the chamber container 6 is completely filled with blood 4. This is associated with a frequency spectrum above it, which again shows the pressure amplitude 36 on its ordinate and the frequency 40 on the abscissa. It can be seen that the pressure amplitude 36 of the first frequency spectrum is very pronounced and slowly decreases with increasing frequency 40, i.e. with frequency spectra located further to the left. In the middle fill state, the blood 4 in the chamber container 6 is half filled and the right chamber container 6 is bloodless. Again, it can be seen that in the middle fill state, the pressure amplitude 36 is already less pronounced than in the completely filled state shown on the left. In the completely emptied state, shown on the far right, the pressure amplitude 36 is even less pronounced. It is therefore obvious that the frequency spectrum permits a clear assignment to the respective fill state of the chamber container 6.

Figure 6:
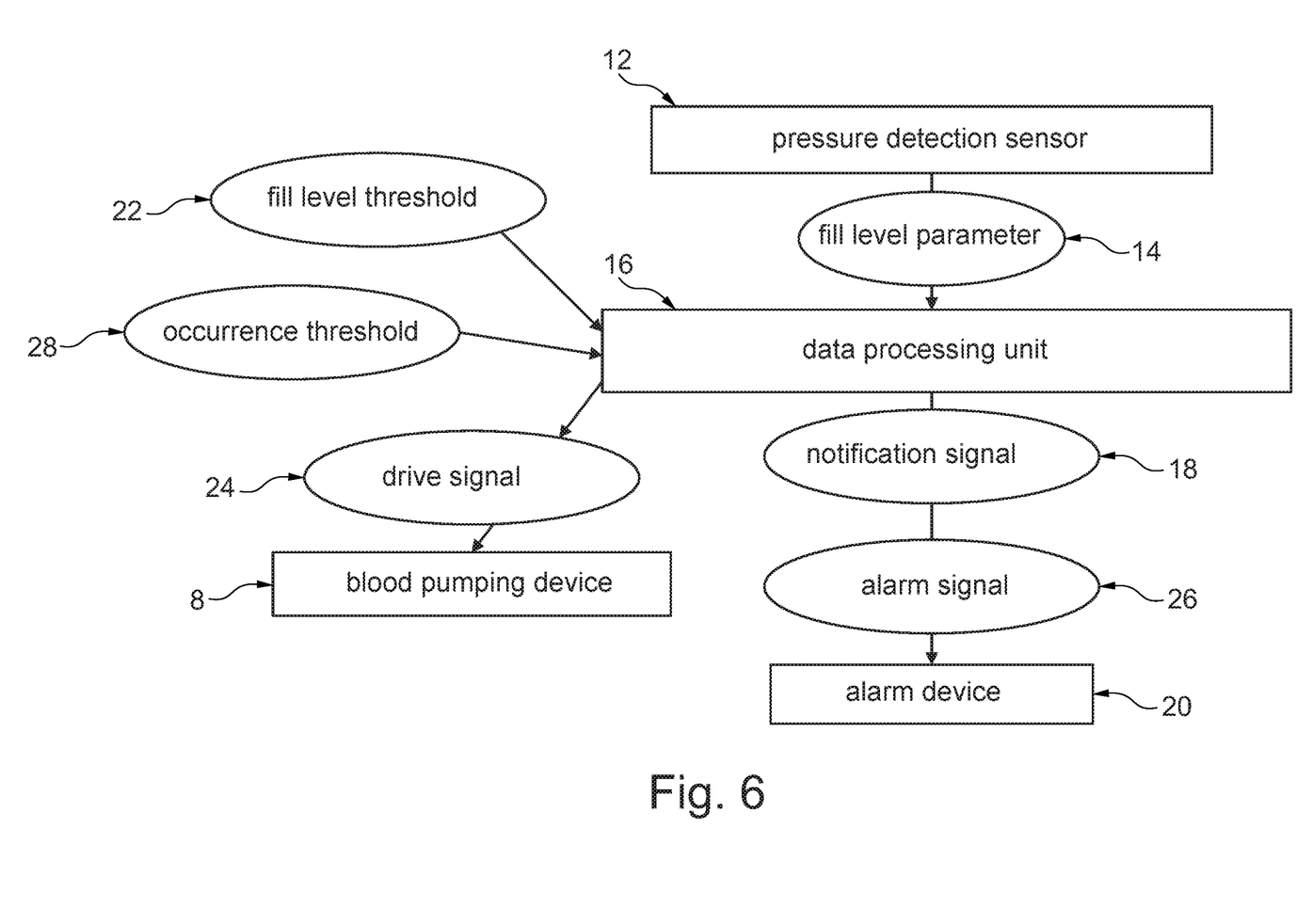
FIG. 6 shows the thresholds and parameters processed by the data processing unit and the signals sent to the respective output devices.

FIG. 6 shows a data processing unit 16, which receives a fill level parameter 14 from the pressure detection sensor 12. The data processing unit 16 processes the received fill level parameter 14 under consideration of the fill level threshold 22 to a notification signal 18, which is set to an activated or a deactivated state, respectively, or to an alarm signal 26, which can also be set to an activated or deactivated state to activate the alarm device 20. Furthermore, the data processing unit 16 is given an occurrence threshold 28, which defines how often the blood pumping device 8 may refill the chamber container 6 in order to still be in a damage-free state and not have any leakage. If the occurrence threshold 28 is exceeded, an alarm signal 26 is output to activate the alarm device 20. If the fill level of the chamber container/air separator falls below the fill level threshold 22, a control signal 24 is generated, which is adapted to activate the pumping device 8 to refill the chamber container 6 with blood 4.

In the following, the method steps are mentioned which are necessary to recognize how the frequency spectrum changes in detail depending on the chamber size and the chamber material (this is also known under the term that different 'bloodlines' are recognized).

The basic idea of the method according to the invention is to close the venous clamp before priming, i.e. when there is only air in the line, and then to pump in a fixed amount of air via the blood pump. For this purpose, the blood pumping device (pump) can be set in advance to a position that allows it to pump, for example, exactly one revolution with a known fluid quantity. In this case, the start position of the roller is just still engaged on the pump output side. The amount of blood to be pumped is approx. 10-15 ml per revolution depending on the respective blood pumping device. The venous chamber (20-40 ml), the dialyzer (80-120 ml) and the tube (approx. 10 ml) have a combined volume of approx. 110-170 ml. For a known dialyzer, the volume of the chamber can be calculated from the pressure increase, and for a known blood conducting system, the blood-side fill volume of the dialyzer can be calculated. The basis for this is that the equation of state of ideal gases applies, which states that the (pressure×volume)/temperature=constant, or in mathematical terms: P×V/Temp=const. The total volume of the dialyzer+chamber must be determined, from which the priming volume can then be determined and optimized. The determined volume in addition to an assumption for the remaining tube is typically 4×25 ml/m=100 ml/m+determined volume for the chamber and for the dialyzer. The formulas listed below apply, with the following nomenclature and assumptions:

Vk=chamber volume
Vd=dialyzer volume
VL=air bolus to increase pressure
P=pressure in the respective volume
Assumption: the volume inside the tube is neglected
The following formula apparatus is to be used:
P1×(V1+VL)/T=P2×(V1)/T
V1=Vd+Vk+VL
P1V1+P1VL=P2V1 (wherein the assumption is: temp=const; V1+VL is compressed to V1)
P1VL=P2V1−P1V1
P1VL/V1=P2−P1
V1=P1VL/(P2−P1)
Vd+Vk+VL=P1VL/(P2−P1)
Vk=P1VL/(P2−P1)−Vd−VL Furthermore, the treatment device 1 may have the monitoring functions, device features, or states listed below:

Fill level monitoring of the air separator of a dialysis machine, a device for determining the fill level of the air separator via the pressure curve, a device for determining the arterial or respectively venous pressure curve, a method for determining the fill level of the air separator, a method for determining the arterial or respectively venous pressure curve, the determination of the fill level by frequency analysis of the pressure curve, the determination of the fill level by introduction of a certain amount of air or liquid and evaluation of the pressure increase, the introduction of the air through connections gage-increase/gage-lowering with standing blood pump and closed SAKV, the introduction of the air or liquid through the blood pump with closed SAKV, comparison of the pressure curve with a reference state, storing the reference state as a fixed value, determination of the reference state in the filled state, alarming in case of certain deviation from the reference state, automatic readjustment of the fill state in case of deviation from the reference state, the alarming in case of too frequent readjustment of the filled state, a device for detecting foam in the air separator, a device for determining the amount of foam and blood, a method for detecting foam in the air separator, a method for determining the amount of foam in the blood and/or a device for detecting the blood tube systems used.

The invention claimed is:

1. A blood treatment device for extracorporeal blood treatment, comprising a blood conducting system with a chamber container for separating bubbles from a blood to be treated, and a blood pumping device configured to pump the blood and which in addition generates a pressure pulse with a predefined frequency in the blood conducting system,
    wherein
    the blood treatment device further comprises:
    a pressure detection sensor in the blood conducting system for detecting the pressure pulse introduced by the blood pumping device,
    a data processing unit which is adapted to determine a pressure pulse amplitude and/or a pressure pulse width of the pressure pulse from the detected pressure pulse, which serve as a fill level parameter, to compare the pressure pulse width and/or the pressure pulse amplitude with at least one reference value stored in the data processing unit to determine a fill level of the blood in the chamber container based on a comparison with the at least one reference value, and to change a state of a notification signal as a function of the fill level parameter and thus the fill level of the blood in the chamber container,
    at least one alarm device which is activated as a function of the state of the notification signal.

2. The blood treatment device according to claim 1, wherein the pressure pulse detected after a first filling of the chamber container with the blood or a previously determined pressure pulse which represents a state of the chamber container completely filled with blood is stored in the data processing unit as the at least one reference value, and at a predetermined maximum deviation between the pressure pulse width of the pressure pulse and the pressure pulse width of the at least one reference value and/or a predetermined maximum deviation between the pressure pulse amplitude of the pressure pulse and the pressure pulse amplitude of the at least one reference value, the data processing unit changes the state of the notification signal.

3. The blood treatment device according to claim 1, wherein a pressure pulse of the chamber container at a predefined fill level threshold is stored as the at least one reference value in the data processing unit and, the data processing unit changes the state of the notification signal when a predetermined minimum deviation between the pressure pulse width of the pressure pulse and the pressure pulse width of the at least one reference value or an overshoot and/or a predetermined minimum deviation between the pressure pulse amplitude of the pressure pulse and the pressure pulse amplitude of the at least one reference value or an undershoot.

4. The blood treatment device according to claim 1, wherein the blood treatment device, in its blood conducting system, consists of exactly one pressure detection sensor and with said one pressure detection sensor is able to determine the fill level height of blood in the chamber container.

5. The blood treatment device according to claim 1, wherein the data processing unit is adapted to perform a frequency analysis method for determining the pressure amplitude and the pressure width from the pressure pulse.

6. The blood treatment device according to claim 5, wherein a pressure pulse formed as a frequency spectrum is stored in the data processing unit as the at least one reference value or the data processing unit is adapted to convert a pressure pulse stored in the data processing unit into a stored frequency spectrum via a frequency analysis method, and the data processing unit is adapted to compare the frequency spectrum of the pressure pulsewidth the stored frequency spectrum and to change the state of the notification signal when a predetermined minimum deviation and/or a predetermined maximum deviation occurs.

7. The blood treatment device according to claim 5,
wherein at least one predetermined frequency amplitude or frequency range amplitude is stored as the at least one reference value, and
wherein the data processing unit changes the state of the notification signal when the at least one predetermined frequency amplitude or frequency range amplitude is undershot.

8. The blood treatment device according to claim 7, wherein a frequency amplitude at a predefined fill level threshold is stored as the at least one reference value.

9. The blood treatment device according to claim 1,
wherein the fill level parameter represents a measure for the fill level of the blood in the chamber container, and
wherein the data processing unit is adapted to change the notification signal to a first relevant state as soon as the fill level parameter falls below a predefined fill level threshold.

10. The blood treatment device according to claim 9, wherein the data processing unit is additionally adapted to generate a drive signal when the notification signal is changed to the first relevant state, and
wherein the drive signal drives the blood pumping device in such a way that the fill level of the blood in the chamber container is increased as soon as the predefined fill level threshold is undershot.

11. The blood treatment device according to claim 10, wherein the data processing unit is additionally adapted to change an alarm signal into a second relevant state and to activate the at least one alarm device as soon as a predefined occurrence threshold, which defines how often the fill level of the blood in the chamber container falls below the fill level threshold in a predefined time interval, is exceeded.

12. The blood treatment device according to claim 1, wherein the pressure detection sensor has a sampling rate of at least 100 Hz to detect the pressure pulse of the blood over time.

13. The blood treatment device according to claim 1,
wherein the blood pumping device additionally comprises a gage and/or level regulation pump, and
wherein the chamber container additionally comprises a drivable ventilation opening for ventilating the chamber container.

14. A method for monitoring the fill level of blood in the blood treatment device according to one of claim 1, comprising the following steps:
detecting the pressure pulse-introduced by the blood pumping device by the pressure detection sensor;
determining the pressure pulse amplitude and/or the pressure pulse width of the pressure pulse as the fill level parameter;
comparing the pressure pulse width and/or pressure pulse amplitude with the at least one reference value stored in the data processing unit;
determining the fill level of the blood in the chamber container based on the comparison with the at least one reference value;
continuously analyzing and processing the fill level parameter by the data processing unit;
changing the state of the notification signal based on the fill level parameter as soon as the fill level falls below a predefined fill level threshold; and
activating the alarm device based on the state of the notification signal.

15. The method according to claim 14, further comprising the step of continuously determining the pressure pulse amplitude and/or the pressure pulse width from the pressure pulse via a frequency analysis method by the data processing unit.

16. The method according to claim 14, further comprising the steps of:
changing a state of an alarm signal to a relevant state as soon as the predefined fill level threshold exceeds a predefined occurrence threshold; and
activating the alarm device when the state of the alarm signal is changed to the relevant state.

* * * * *